US010087123B2

(12) United States Patent
Shin et al.

(10) Patent No.: US 10,087,123 B2
(45) Date of Patent: Oct. 2, 2018

(54) METHOD FOR PREPARING OLEFIN OLIGOMERS IN THE PRESENCE OF A HALOGENATED ORGANIC SOLVENT AND A CATALYST COMPRISING TWO DIPHOSPHINO AMINE COMPOUNDS

(71) Applicant: LG CHEM, LTD., Seoul (KR)

(72) Inventors: Eun Ji Shin, Daejeon (KR); Yong Ho Lee, Daejeon (KR); Seok Pil Sa, Daejeon (KR); Ki Soo Lee, Daejeon (KR); Jin Young Park, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/023,632

(22) PCT Filed: Jun. 12, 2015

(86) PCT No.: PCT/KR2015/005953
§ 371 (c)(1),
(2) Date: Mar. 21, 2016

(87) PCT Pub. No.: WO2015/194801
PCT Pub. Date: Dec. 23, 2015

(65) Prior Publication Data
US 2016/0207850 A1 Jul. 21, 2016

(30) Foreign Application Priority Data

Jun. 18, 2014 (KR) .................. 10-2014-0074368
Jun. 8, 2015 (KR) .................. 10-2015-0080718

(51) Int. Cl.
*C07C 2/32* (2006.01)
*B01J 31/12* (2006.01)
*B01J 31/14* (2006.01)
*B01J 31/18* (2006.01)
*C07C 2/36* (2006.01)
*C08F 10/02* (2006.01)

(52) U.S. Cl.
CPC ............... *C07C 2/32* (2013.01); *B01J 31/12* (2013.01); *B01J 31/143* (2013.01); *B01J 31/186* (2013.01); *C07C 2/36* (2013.01); *C08F 10/02* (2013.01); *B01J 2231/20* (2013.01); *B01J 2531/0205* (2013.01); *B01J 2531/62* (2013.01); *C07C 2531/14* (2013.01); *C07C 2531/18* (2013.01); *C07C 2531/22* (2013.01); *C07C 2531/24* (2013.01)

(58) Field of Classification Search
CPC ......... C07C 2/32; C07C 2/36; C07C 2531/18; C07C 2531/22; C07C 2531/14; C07C 2531/24; C08F 10/02; B01J 31/186; B01J 31/143; B01J 31/12; B01J 2531/0205; B01J 2231/20; B01J 2531/62
See application file for complete search history.

(56) References Cited

U.S. PATENT DOCUMENTS

| | | | |
|---|---|---|---|
| 8,076,523 B2 | 12/2011 | Bollmann et al. | |
| 8,334,420 B2 | 12/2012 | Small et al. | |
| 2003/0166456 A1 | 9/2003 | Wass | |
| 2007/0185363 A1 | 8/2007 | Bercaw et al. | |
| 2007/0232481 A1 | 10/2007 | Zhang et al. | |
| 2008/0027188 A1* | 1/2008 | Small ............... | B01J 31/143 526/113 |
| 2008/0058486 A1 | 3/2008 | McCullough et al. | |
| 2009/0118117 A1 | 5/2009 | Elowe et al. | |
| 2010/0081842 A1 | 4/2010 | Gao et al. | |
| 2012/0310025 A1 | 12/2012 | Wang et al. | |
| 2012/0316303 A1 | 12/2012 | Hanton et al. | |

FOREIGN PATENT DOCUMENTS

| | | | | |
|---|---|---|---|---|
| CN | 1630554 A | 6/2005 | | |
| CN | 1651142 A | 8/2005 | | |
| CN | 101415494 A | 4/2009 | | |
| CN | 101450326 A | 6/2009 | | |
| CN | 101511851 A | 8/2009 | | |
| CN | 102164936 A | 8/2011 | | |
| CN | 103285926 A | 9/2013 | | |
| JP | 2004502527 A | 1/2004 | | |
| JP | 2013515601 A | 5/2013 | | |
| WO | 2013168103 A1 | 11/2013 | | |
| WO | WO-2015083053 A1 * | 6/2015 | ............... | C07C 2/34 |

OTHER PUBLICATIONS

Paul R. Elowe, et al., Nitrogen-Linked Diphoshine Ligands with Ethers Attached to Nitrogen for Chromium-Catalyzed Ethylene Tri - and Tetramerizations, Organometallics, 2006, 25, 5255-5260.

* cited by examiner

*Primary Examiner* — In Suk C Bullock
*Assistant Examiner* — Ali Z Fadhel
(74) *Attorney, Agent, or Firm* — Dentons US LLP

(57) ABSTRACT

The present invention relates to a process for preparing an olefin oligomer including a step of contacting an olefin monomer with a composite catalyst in the presence of a halogenated organic solvent, wherein the composite catalyst includes: a transition metal compound; a cocatalyst; and an organic ligand including a diphosphonoamine compound in which two or more diphosphonoamines are combined via a polyvalent functional group.

10 Claims, No Drawings

METHOD FOR PREPARING OLEFIN OLIGOMERS IN THE PRESENCE OF A HALOGENATED ORGANIC SOLVENT AND A CATALYST COMPRISING TWO DIPHOSPHINO AMINE COMPOUNDS

CROSS-REFERENCE TO RELATED APPLICATION(S)

This application is a National Stage Application of International Application No. PCT/KR2015/005953, filed Jun. 12, 2015, and claims the benefit of Korean Patent Application No. 10-2015-0080718 filed Jun. 8, 2015, and Korean Patent Application No. 10-2014-0074368, filed Jun. 18, 2014, the contents of which are incorporated by reference in their entirety for all purposes as if fully set forth below.

TECHNICAL FIELD

The present invention relates to a process for preparing an olefin oligomer, and more particularly to a process for preparing an olefin oligomer that has improved reaction activity and selectivity of the catalyst components used and that also oligomerizes an olefin monomer more easily and economically.

BACKGROUND OF ART

Linear alpha-olefins are important substances which are used for comonomers, detergents, lubricants, plasticizers, etc., and are widely used for commercial purposes. In particular, 1-hexene and 1-octene are frequently used as comonomers for controlling the density of polyethylene in the preparation process of linear low-density polyethylene (LLDPE).

The conventional processes for preparing LLDPE include copolymerizing ethylene with alpha-olefins, for example a comonomer such as 1-hexene or 1-octene, in order to control the density of the polyethylene by forming branches to the polymer backbone. In order to increase the content of comonomers such as 1-hexene, 1-octene, or the like in LLDPE to be synthesized, there was a problem that the production costs increase. Thus, various studies regarding a method for providing the comonomer in a more economical and easy manner have been performed.

The existing commercial processes for preparing 1-hexene or 1-octene may include a SHOP process by Shell Chemical, a Ziegler Process by Chevron Philips, and the like. Using these processes, an alpha-olefin having 4 to 20 carbon atoms can be produced.

Specifically, a catalyst for ethylene oligomerization which includes an organic ligand compound containing a transition metal such as chromium, etc., any one element of phosphorus, arsenic, and antimony, and nitrogen has been known in the art.

Since the alpha-olefin has different application fields or market sizes depending on its type, a technique capable of selectively producing a certain type of olefin is commercially very important. Recently, studies regarding catalyst technology utilizing a transition metal such as chromium to prepare 1-hexene or 1-octene with high selectivity through selective ethylene oligomerization or multimerization have been frequently performed.

Thus, there is a need to develop a process capable of securing high activity and high selectivity for a long period of time in current reaction procedures and oligomerizing olefin monomers in a more economical and easy manner.

DETAILED DESCRIPTION OF THE INVENTION

Technical Problem

It is an object of the present invention to provide a process for preparing an olefin oligomer that is capable of improving reaction activity and selectivity of the catalyst components used, and also oligomerizing an olefin monomer more easily and economically.

Technical Solution

There is provided a process for preparing an olefin oligomer including a step of contacting an olefin monomer with a composite catalyst in the presence of a halogenated organic solvent, wherein the composite catalyst includes: a transition metal compound; a cocatalyst; and an organic ligand including a diphosphinoamine compound in which two or more diphosphinoamines are combined via a polyvalent functional group.

Hereinafter, the process for preparing an olefin oligomer according to specific embodiments of the invention will be described in more detail.

As used herein, the olefin oligomer refers to a compound formed by multimerization, e.g., dimerization, trimerization, or tetramerization of an olefin monomer such as ethylene. Specifically, the olefin oligomer may be an alkene having 4 to 10 carbon atoms or an alpha-olefin having 4 to 10 carbon atoms.

According to one embodiment of the invention, a process for preparing an olefin oligomer including a step of contacting an olefin monomer with a composite catalyst in the presence of a halogenated organic solvent can be provided, wherein the composite catalyst includes: a transition metal compound; a cocatalyst; and an organic ligand including a diphosphinoamine compound in which two or more diphosphinoamines are combined via a polyvalent functional group.

The present inventors found through numerous experiments that when a halogenated organic solvent is introduced or used in the step of contacting the olefin monomer with the composite catalyst, it is possible to improve the reaction activity and selectivity of the catalyst components used and also oligomerize the olefin monomer more easily and economically. The present invention has been completed on the basis of such a finding.

Also, by using a composite catalyst which includes an organic ligand containing a diphosphinoamine compound in which two or more diphosphinoamines are combined via a polyvalent functional group, the oligomers such as 1-hexene and/or 1-octene may be provided from the olefin monomer such as ethylene, etc. with higher efficiency and selectivity, and also the content of by-products such as polyethylene in the final product can be minimized by preventing the polymerization.

The halogenated organic solvent may be an aliphatic compound substituted by one or more halogen atoms, an alicyclic compound substituted by one or more halogen atoms, or an aromatic compound substituted by one or more halogen atoms.

Specifically, the halogenated organic solvent may include one or more organic solvents selected from the group consisting of a straight-chain or branched alkane having 1 to 20 carbon atoms which is substituted by one or more halogen atoms, an arene having 6 to 20 carbon atoms which is substituted by one or more halogen atoms, and a cycloalkane having 4 to 20 carbon atoms which is substituted by one or more halogen atoms.

More specifically, the halogenated organic solvent may include chlorobenzene, dichlorobenzene, or both thereof.

In the process for preparing an olefin oligomer according to the above-described embodiment, the used amount of the halogenated organic solvent is not particularly limited, and may be determined in consideration of the reaction conditions in the step of contacting the composite catalyst with the olefin monomer, or the kind and weight of the reactants used in this step.

For example, the halogenated organic solvent may be used in a weight ratio of 0.1 to 100 times or 0.5 to 10 times relative to the weight of the olefin oligomer finally prepared.

In the process for preparing the olefin oligomer, in order to more efficiently prepare the olefin oligomer from the olefin monomer, the transition metal compound may include chromium or a chromium-containing compound. Specifically, the transition metal compound may include chromium, an inorganic chromium salt, an organic chromium salt, an organic chromium metal complex, or a mixture of two or more thereof.

More specifically, the chromium-containing compound may include chromium (III) acetylacetonate, chromium trichloride tris-tetrahydrofuran, (benzene)tricarbonyl chromium, chromium (III) butyrate, chromium (III) pentanoate, chromium (III) laurate, chromium (III) stearate, chromium (III) octanoate, chromium hexacarbonyl, chromium (III) 2-ethyl hexanoate, or a mixture of two or more thereof.

On the other hand, the above-described composite catalyst may include a cocatalyst, and as the cocatalyst, any cocatalyst known to be usable in the transition metal-containing catalyst may be used without particular limitation.

Specific examples of the cocatalyst may include one or more selected from the group consisting of the compounds of the following Chemical Formulae 11 to 13 and the modified methylaluminoxane.

[L-H]$^+$[Z(E)$_4$]$^-$ or [L]$^+$[Z(E)$_4$]$^-$      [Chemical Formula 11]

In the above Chemical Formula 11, L is a neutral or cationic Lewis base, [L-H]+ or [L]$^+$ is a Brønsted acid, H is a hydrogen atom, Z is a group 13 element, and each E may be the same as or different from each other and each is independently an aryl group having 6 to 20 carbon atoms or an alkyl group having 1 to 20 carbon atoms, in which one or more hydrogen atoms are unsubstituted or substituted by a halogen, a hydrocarbyl having 1 to 20 carbon atoms, an alkoxy functional group, or a phenoxy functional group.

D(R$_9$)$_3$      [Chemical Formula 12]

In the above Chemical Formula 12, D is aluminum or boron, each R$_9$ may be the same as or different from each other, and each is independently a halogen, a hydrocarbon group having 1 to 20 carbon atoms, or a hydrocarbon group having 1 to 20 carbon atoms which is substituted by a halogen.

[Chemical Formula 13]

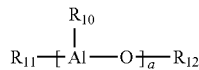

In the above Chemical Formula 13, R$_{10}$, R$_{11}$, and R$_{12}$ may be the same as or different from each other, and are each hydrogen, a halogen group, an aliphatic hydrocarbon group having 1 to 20 carbon atoms, or an aliphatic hydrocarbon group having 1 to 20 carbon atoms which is substituted by a halogen, and a is an integer of 2 or more.

The compound of Chemical Formula 11 may serve to activate a transition metal compound of Chemical Formula 1, and may include a non-coordinating anion that is compatible with a cation which is a Brönsted acid.

Preferably, the anion has a relatively large size and includes a single coordination complex containing a metalloid.

In particular, the compound containing a single boron atom in the anion part is widely used.

From these viewpoints, the salt having the anion which contains the coordination complex containing a single boron atom is preferred.

In the composite catalyst, the ratio of moles of the transition metal compound to moles of the compound of Chemical Formula 11 may be 1:1 to 1:20, preferably 1:10 to 1:4.

If the mole ratio is less than 1:1, the activation of the metal compound may not be fully achieved due to a relatively small amount of the cocatalyst, thereby resulting in insufficient activity of the transition metal catalyst. If the ratio exceeds 1:20, the activity of the transition metal catalyst may increase, but a problem of a great increase of production costs may occur due to the use of the cocatalyst in an amount that is more than necessary.

Specific examples of the compound of Chemical Formula 11 may include triethylammoniumtetra(phenyl)boron, tributylammoniumtetra(phenyl)boron, trimethylammoniumtetra(phenyl)boron, tripropylammoniumtetra(phenyl)boron, trimethylammoniumtetra(p-tolyl)boron, trimethylammoniumtetra(o,p-dimethylphenyl)boron, tributylammoniumtetra(p-trifluoromethylphenyl)boron, trimethylammoniumtetra(p-trifluoromethylphenyl)boron, tributylammoniumtetra(pentafluorophenyl)boron, N,N-diethylanildiumtetra(phenyl)boron, N,N-diethylanilidiumtetra(phenyl)boron, N,N-diethylaniliniumtetra(pentafluorophenyl)boron, diethylammoniumtetra(pentafluorophenyl)boron, triphenylphosphoniumtetra(phenyl)boron, trimethylphosphoniumtetra(phenyl)boron, triethylammoniumtetra(phenyl)aluminum, tributylammoniumtetra(phenyl)aluminum, trimethylammoniumtetra(phenyl)aluminum, tripropylammoniumtetra(phenyl)aluminum, trimethylammoniumtetra(p-tolyl)aluminum, tripropylammoniumtetra(p-tolyl)aluminum, triethylammoniumtetra(o,p-dimethylphenyl)aluminum, tributylammoniumtetra(p-trifluoromethylphenyl)aluminum, trimethylammoniumtetra(p-trifluoromethylphenyl)aluminum, tributylammoniumtetra(pentafluorophenyl)aluminum, N,N-diethylaniliniumtetra(phenyl)aluminum, N,N-diethylaniliniumtetra(phenyl)aluminum, N,N-diethylaniliniumtetra(pentafluorophenyl)aluminum, diethylammoniumtetra(pentafluorophenyl)aluminum, triphenylphosphoniumtetra(phenyl)aluminum, trimethylphosphoniumtetra(phenyl)aluminum, triethylammoniumtetra(phenyl)aluminum, tributylammoniumtetra(phenyl)aluminum, trimethylammoniumtetra(phenyl)boron, tripropylammoniumtetra(phenyl)boron, trimethylammoniumtetra(p-tolyl)boron, tripropylammoniumtetra(p-tolyl)boron, triethylammoniumtetra(o,p-dimethylphenyl)boron, trimethylammoniumtetra(o,p-dimethylphenyl)boron, tributylammoniumtetra(p-trifluoromethylphenyl)boron, trimethylammoniumtetra(p-trifluoromethylphenyl)boron, tributylammoniumtetra(pentafluorophenyl)boron, N,N-diethylaniliniumtetra (phenyl)boron, N,N-diethylaniliniumtetra(phenyl)boron, N,N-diethylaniliniumtetra(pentafluorophenyl)boron, diethylammoniumtetra(pentafluorophenyl)boron, triphenylphosphoniumtetra(phenyl)boron, triphenylcarboniumtetra(p-trifluoromethylphenyl)boron, triphenylcarboniumtetra (pentafluorophenyl)boron, trityltetra(pentafluorophenyl) boron, and the like, but are not limited thereto.

The compound of Chemical Formula 12 or 13 may play a role of a scavenger to remove a contaminant acting as a poison to the catalyst among the reactants.

In the above composite catalyst, moles of the transition metal compound to moles of the compound of Chemical Formula 12 or 13 may be 1:1 to 1:8,000, and preferably 1:10 to 1:5,000.

When the mole ratio is less than 1:1, the effect of adding the scavenger is trivial. When the mole ratio exceeds 1:5,000, an excessive amount of the alkyl group, etc. retained without participating in the reaction may rather inhibit the catalytic reaction to act as a catalytic poison. According to this, some side reactions occur and there may be a problem that excess aluminum or boron remains in the polymer.

Specific examples of the compound of Chemical Formula 12 may include trimethylaluminum, triethylaluminum, triisobutylaluminum, tripropylaluminum, tributylaluminum, dimethylchloroaluminum, triisopropylaluminum, tri-s-butylaluminum, tricyclopentylaluminum, tripentylaluminum, triisopentylaluminum, trihexylaluminum, trioctylaluminum, ethyldimethylaluminum, methyldiethylaluminum, triphenylaluminum, tri-p-tolylaluminum, dimethylaluminummethoxide, dimethylaluminumethoxide, trimethylboron, triethylboron, triisobutylboron, tripropylboron, tributylboron, preferably trimethylaluminum, triethylaluminum, and triisobutylaluminum.

Specific examples of the compound of Chemical Formula 13 may include the aluminoxane compound containing a straight chain or branched alkyl group having 1 to 6 carbon atoms, such as, for example, methylaluminoxane, ethylaluminoxane, isobutylaluminoxane, and butylaluminoxane, preferably methylaluminoxane.

Further, the above modified methylaluminoxane (MMAO) refers to a compound wherein some of the methyl groups in methyl aluminoxane are substituted by other alkyl group, specifically a compound wherein 40 mol % or less, or 5 mol % to 35 mol % of the alkyl groups in the methyl aluminoxane is substituted by a straight-chain or branched alkyl group having 3 to 10 carbon atoms.

More specific examples of the modified methylaluminoxane may include commercial products such as MMAO-12, MMAO-3A, and MMAO-7.

In the above composite catalyst, moles of the transition metal compound to moles of the above modified methylaluminoxane may be 1:1 to 1:8,000, and preferably 1:10 to 1:5,000.

As described above, as the composite catalyst which includes an organic ligand containing a diphosphinoamine compound wherein two or more diphosphinoamines are combined via a polyvalent functional group is used, the oligomers such as 1-hexene and/or 1-octene may be provided from the olefin monomer such as ethylene with higher efficiency and selectivity, and also the content of by-products such as polyethylene, etc. in the final product can be minimized by preventing the polymerization.

The diphosphinoamine compound wherein two or more diphosphinoamines are combined via a polyvalent functional group may be the diphosphinoamine compound wherein a) two to six diphosphinoamines are combined via a divalent to hexavalent functional group derived from the compound selected from the group consisting of b) a cycloalkane having 4 to 20 carbon atoms which is unsubstituted or substituted by an alkyl group having 1 to 5 carbon atoms or a halogen, a straight-chain or branched alkane having 1 to 20 carbon atoms which is substituted by one or more halogen atoms, and an arene having 6 to 30 carbon atoms which is unsubstituted or substituted by an alkyl group having 1 to 5 carbon atoms or a halogen.

More specifically, the diphosphinoamine compound wherein two or more diphosphinoamines are combined via a polyvalent functional group may be the diphosphinoamine compound including i) one or more divalent functional groups selected from the group consisting of a cycloalkylene having 4 to 20 carbon atoms which is unsubstituted or substituted by an alkyl group having 1 to 5 carbon atoms or a halogen, a straight-chain or branched alkylene having 1 to 20 carbon atoms which is substituted by one or more halogen atoms, and an arylene having 6 to 30 carbon atoms which is unsubstituted or substituted by an alkyl group having 1 to 5 carbon atoms or a halogen, and ii) at least two diphosphinoamine functional groups.

Specific examples of the diphosphinoamine compound in which two or more diphosphinoamines are combined via a polyvalent functional group may include a compound of the following Chemical Formula 1.

[Chemical Formula 1]

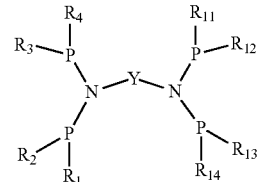

In the above Formula 1, $R_1$, $R_2$, $R_3$, $R_4$, $R_{11}$, $R_{12}$, $R_{13}$, and $R_{14}$ are each an aryl group which has 6 to 20 carbon atoms and is unsubstituted or mono- or polysubstituted by one or more functional groups selected from the group consisting of a halogen, an alkyl group having 1 to 10 carbon atoms, and an alkoxy group having 1 to 5 carbon atoms, and Y is a cycloalkylene unsubstituted or mono- or polysubstituted by an alkyl group having 1 to 5 carbon atoms, a straight-chain or branched alkylene having 1 to 20 carbon atoms which is mono- or polysubstituted by a halogen atom, or an arylene having 6 to 30 carbon atoms which is unsubstituted or mono- or polysubstituted by an alkyl group having 1 to 5 carbon atoms.

Specifically, Y may be a divalent functional group having the following Chemical Formula 2.

[Chemical Formula 2]

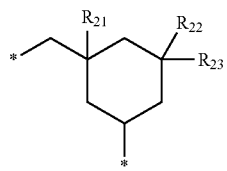

In the above Formula 2, $R_{21}$, $R_{22}$, and $R_{23}$ each are hydrogen, a halogen, or a straight-chain or branched alkyl group having 1 to 4 carbon atoms, and * means a binding point.

On the other hand, the above organic ligand compound may further include any organic ligand compound known to be usable in the preparation of an olefin oligomer, in addition to the diphosphinoamine compound wherein two or more diphosphinoamines are combined via a polyvalent functional group.

The mole ratio of the transition metal compound to the above organic ligand compound may be 1:0.5 to 1:20, or 1:1 to 1:10, or 1:1 to 1:5.

If the number of moles of the organic ligand compound is too small in comparison with the number of moles of the transition metal compound, the efficiency or selectivity in the oligomerization of the olefin monomer such as ethylene, etc. may not be sufficient.

Otherwise, if the number of moles of the organic ligand compound is too large in comparison with the number of moles of the transition metal compound, the organic ligand compound may unnecessarily exist in an excessive amount in the composite catalyst.

On the other hand, the step of reacting the composite catalyst and the olefin monomer may utilize a conventional apparatus and method known to be usable in the oligomerization reaction of an olefin monomer.

The reaction of the composite catalyst and the olefin monomer may be performed at a temperature of 0° C. to 200° C., 5° C. to 150° C., or 20° C. to 100° C.

Also, the reaction of the composite catalyst and the olefin monomer may be performed under the pressure condition of 1 bar to 200 bar, or 5 bar to 100 bar.

The olefin monomer may include ethylene, and the ethylene reacted with the composite catalyst may be in a gaseous state.

Advantageous Effects

According to the present invention, a process for preparing an olefin oligomer that is capable of improving reaction activity and selectivity of the catalyst components used and also oligomerizing an olefin monomer more easily and economically, may be provided. Through this process for preparing the olefin oligomer, such olefin oligomers as 1-hexene, 1-octene, other alpha-olefins having 4 to 10 carbon atoms, etc. may be provided with more efficiency.

Detailed Description of the Embodiments

Embodiments of the invention will be explained in more detail by way of the following examples. However, these examples are provided only for illustration of the invention, and should not be construed as limiting the invention.

Examples and Comparative Examples: Preparation of Olefin Oligomers

Example 1

(1) Preparation of Composite Catalyst for Olefin Oligomerization

Under an argon gas atmosphere, chromium (III) acetylacetonate [Cr(acac)$_3$] (17.5 mg, 0.05 mmol) and the organic ligand of the following Chemical Formula 1-1 (0.0275 mmol) were introduced into a flask. 10 mL of cyclohexane was then added thereto and stirred to give 5 mM of a composite catalyst solution (S1).

[Mole ratio of free ligand to Cr is 0.55:1]

[Chemical Formula 1-1]

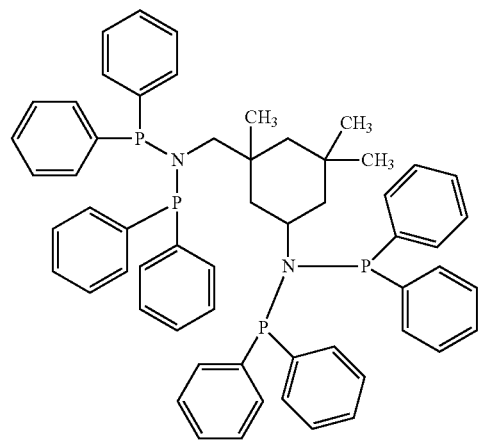

(2) Preparation of Olefin Oligomer

A 600 mL volume Parr reactor was subjected to vacuum treatment at 120° C. for 2 h, the temperature of the reactor was lowered to 60° C. and the inside thereof was refilled with argon.

Thereafter, 90 mL of chlorobenzene and 2 mL of modified methylaluminoxane (7 wt % isoheptane solution) were introduced, and 1 mL (5 μmol) of the 5 mM solution (S1) was introduced to the reactor.

At this time, an Al/Cr ratio in the solutions introduced to the reactor was 1200.

Cyclohexane, the modified methylaluminoxane, and the solution (S1) in the reactor were stirred for 2 min at 500 rpm, the inside of the reactor was filled with ethylene by opening a valve of an ethylene line which was set to 60 bar, and then the mixture was stirred for 15 min at 500 rpm.

After the stirring, the valve of the ethylene line was closed, the temperature was adjusted to 0° C., the reactor was cooled in a dryice/acetone bath, and after venting, 0.5 mL of nonane (GC internal standard) was added.

Then, 2 mL of the liquid part of the reactor was taken and quenched with water, and the organic part was filtered through a PTFE syringe filter to give a GC sample.

This GC sample was analyzed by GC.

Further, 400 mL of ethanol/HCl (10 vol % of 12 M aqueous HCl solution) was added to the remaining reaction solution and filtered to give a polymer.

Thus obtained polymer was dried overnight in a 60° C. vacuum oven and the final weight was measured.

Example 2

The olefin oligomer was prepared according to the same procedure as in Example 1, except that 90 mL of 1,2-dichlorobenzene was used instead of 90 mL of chlorobenzene.

Comparative Example 1

The olefin oligomer was prepared according to the same procedure as in Example 1, except that 90 mL of pentane was used instead of 90 mL of chlorobenzene.

Comparative Example 2

The olefin oligomer was prepared according to the same procedure as in Example 1, except that 90 mL of toluene was used instead of 90 mL of chlorobenzene.

Comparative Example 3

The olefin oligomer was prepared according to the same procedure as in Example 1, except that the organic ligand of $(C_6H_5)_2PN((2\text{-}OCH_3)C_6H_4)P(C_6H_5)_2$ [the following Chemical Formula A] was used instead of the organic ligand of Chemical Formula 1-1.

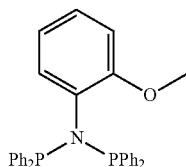

[Chemical Formula A]

The results of the preparation process of olefin oligomers in the examples and comparative examples are shown in Table 1 below.

TABLE 1

| | Ornganic solvent | Reaction activity (Kg/mol Cr/h) | 1-Hexene | 1-Octene | C10-C40 Olefin oligomer | sum | Polyethylene wax |
|---|---|---|---|---|---|---|---|
| Ex. 1 | Chlorobenzene | 100,628 | 29.5 | 56.7 | 6.7 | 92.9 | 1.32 |
| Ex. 2 | 1,2-Dichlorobenzene | 48,391 | 2.1 | 60.5 | 7.1 | 90.7 | 1.88 |
| Comp. Ex. 1 | Cyclohexane | 7,961 | 20.9 | 60.5 | 8.5 | 89.8 | 0.4 |
| Comp. Ex. 2 | Toluene | 2,665 | 15.1 | 52.0 | 14.8 | 81.9 | 2.6 |
| omp. Ex. 3 | Chlorobenzene | 91,949 | 27.6 | 52.9 | 7.9 | 88.4 | 1.74 |

Preparation Product (wt %)

As shown in Table 1 above, it was confirmed that Examples 1 and 2 of preparing the olefin oligomer by contacting the gaseous ethylene and the composite catalyst solution in the presence of chlorobenzene or 1,2-dichlorobenzene not only exhibited higher reaction activity but could also synthesize 1-hexene and 1-octene with higher yield and selectivity.

On the contrary, Comparative Examples 1 and 2 showed considerably lower reaction activity than Example 1. Furthermore, it was confirmed that the content of 1-hexene in the final product was relatively small, whereas that of the olefin oligomer having 10 to 40 carbon atoms was relatively large.

In addition, when the olefin oligomer was prepared by contacting the gaseous ethylene and the composite catalyst solution using the diphosphinoamine of Comparative Example 3 as a ligand, higher catalytic activity than Comparative Examples 1 and 2 was secured, but the reaction activity was still lower than Example 1. Further, it was confirmed in Comparative Example 3 that the content of 1-hexene in the final product was relatively smaller than Example 1, whereas the olefin oligomer having 10 to 40 carbon atoms was obtained in a relatively larger content than Example 1.

What is claims:

1. A process for preparing an olefin oligomer comprising:
contacting an olefin monomer with a composite catalyst in the presence of a halogenated organic solvent to prepare the olefin oligomer;
wherein the composite catalyst comprises a transition metal compound, a cocatalyst, and an organic ligand having a diphosphinoamine compound in which two diphosphinoamines are combined via a polyvalent functional group having the following Chemical Formula 1,

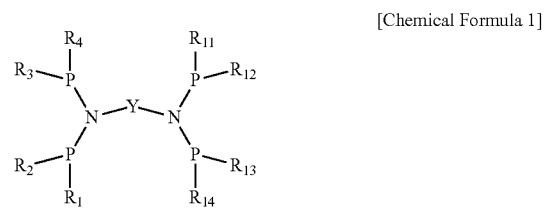

[Chemical Formula 1]

wherein $R_1$, $R_2$, $R_3$, $R_4$, $R_{11}$, $R_{12}$, $R_{13}$, and $R_{14}$ are each an aryl group having 6 to 20 carbon atoms and is unsubstituted or mono- or polysubstituted by one or more functional groups selected from the group consisting of a halogen, an alkyl group having 1 to 10 carbon atoms, and an alkoxy group having 1 to 5 carbon atoms, and Y is a divalent functional group having the following Chemical Formula 2,

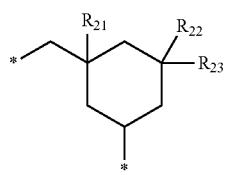

[Chemical Formula 2]

wherein $R_{21}$, $R_{22}$, and $R_{23}$ each are hydrogen, a halogen, or a straight-chain or branched alkyl group having 1 to 4 carbon atoms, and wherein * is a binding point.

2. The process for preparing an olefin oligomer according to claim 1, wherein
the halogenated organic solvent includes one or more organic solvents selected from the group consisting of an arene which has 6 to 20 carbon atoms and is substituted by one or more halogen atoms, a cycloalkane having 4 to 20 carbon atoms and is substituted by one or more halogen atoms, and a straight-chain or branched alkane having 1 to 20 carbon atoms which is substituted by one or more halogen atoms.

3. The process for preparing an olefin oligomer according to claim 1, wherein the halogenated organic solvent comprises chlorobenzene and/or dichlorobenzene.

4. The process for preparing an olefin oligomer according to claim 1, wherein the olefin monomer includes a gaseous ethylene.

5. The process for preparing an olefin oligomer according to claim 1, wherein the transition metal compound includes one or more compounds selected from the group consisting of chromium, an inorganic chromium salt, an organic chromium salt, and an organic chromium metal complex.

6. The process for preparing an olefin oligomer according to claim 1, wherein the transition metal compound includes one or more compounds selected from the group consisting of chromium (III) acetylacetonate, chromium trichloride tris-tetrahydrofuran, (benzene)tricarbonyl chromium, chromium (III) butyrate, chromium (III) pentanoate, chromium (III) laurate, chromium (III) stearate, chromium (III) octanoate, chromium hexacarbonyl, and chromium (III) 2-ethyl hexanoate.

7. The process for preparing an olefin oligomer according to claim 1, wherein a mole ratio of the organic ligand compound to the transition metal contained in the transition metal compound is 1:0.5 to 1:20.

8. The process for preparing an olefin oligomer according to claim 1, wherein the cocatalyst includes one or more compounds selected from the group consisting of the compounds of the following Chemical Formulae 11 to 13 and modified methylaluminoxane:

$$[L\text{-}H]^+[Z(E)_4]^- \text{ or } [L]^+[Z(E)_4]^- \qquad \text{[Chemical Formula 11]}$$

wherein, in the above Formula 11,

L is a neutral or cationic Lewis base,

[L-H]+ or [L]+ is a Brønsted acid,

H is a hydrogen atom,

Z is a group 13 element, and each E may be the same as or different from each other and each is independently an aryl group having 6 to 20 carbon atoms or an alkyl group having 1 to 20 carbon atoms, in which one or more hydrogen atoms are unsubstituted or substituted by a halogen, a hydrocarbyl having 1 to 20 carbon atoms, an alkoxy functional group, or a phenoxy functional group, $$D(R_9)_3 \qquad \text{[Chemical Formula 12]}$$

wherein, in the above Formula 12,

D is aluminum or boron, and each $R_9$ may be the same as or different from each other, and each is independently a halogen, a hydrocarbon group having 1 to 20 carbon atoms, or a hydrocarbon group having 1 to 20 carbon atoms which is substituted by a halogen,

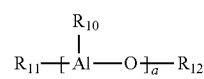

[Chemical Formula 13]

wherein, in the above Formula 13, $R_{10}$, $R_{11}$, and $R_{12}$ may be the same as or different from each other, and each is hydrogen, a halogen, an aliphatic hydrocarbon group having 1 to 20 carbon atoms, or an aliphatic hydrocarbon group having 1 to 20 carbon atoms which is substituted by a halogen, and $a$ is an integer of 2 or more.

9. The process for preparing an olefin oligomer according to claim 1, wherein contacting the composite catalyst and the olefin monomer is performed at a temperature of 0° C. to 200° C.

10. The process for preparing an olefin oligomer according to claim 1, wherein the contacting the composite catalyst and the olefin monomer is performed under a pressure of 1 bar to 200 bar.

* * * * *